United States Patent [19] [11] 4,187,307
Paris et al. [45] Feb. 5, 1980

[54] DIURETICS

[75] Inventors: Gerard Y. Paris, Duvernay; Denis G. Cimon, Montreal-Nord; Dilbagh S. Bariana, Pointe-Claire; Anthony Fung, Pierrefonds, all of Canada

[73] Assignee: Abbott Laboratories, Chicago, Ill.

[21] Appl. No.: 951,935

[22] Filed: Oct. 16, 1978

[51] Int. Cl.² ................. A61K 31/505; C07D 475/06
[52] U.S. Cl. .................................... 424/251; 544/258
[58] Field of Search ......................... 544/258; 424/251

[56] References Cited
PUBLICATIONS

Temple et al., *J. Het. Chem.*, 1970, 7(5), pp. 1195–1197.
Weinstock et al., *J. Med. Chem.*, 1968, 11(3), pp. 573–579.

*Primary Examiner*—Paul M. Coughlan, Jr.
*Attorney, Agent, or Firm*—Paul D. Burgauer; Robert L. Niblack

[57] ABSTRACT

Specific 4-amino pteridines carrying particular phenyl substituents in the 7-position and no substituents in the 2-position have been found to be excellent nonkaliuretic diuretics at doses of 30 to 500 mg/kg in warm-blooded animals.

21 Claims, No Drawings

DIURETICS

DETAILED DESCRIPTION OF THE INVENTION

Pteridines have been known for several decades and some particular pteridines have been suggested or used as antimalarial or antibacterial drugs. All active pteridines reported carry substituents in the 2-position.

It has been found that 4-amino-7-phenyl-pteridine and phenyl-substituted derivatives thereof carrying only position-specified substituents in the phenyl ring have excellent diuretic activity with the highly desirable advantage of closely maintaining the normal potassium level. The compounds of the present invention are best described by reference to formula I

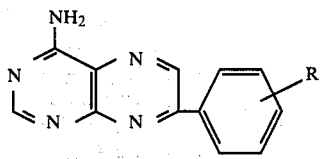

wherein R is chlorine in the o- or m-position, $CH_3$ in the p- or m-position, dimethylamino or H or pharmaceutically acceptable acid addition salts thereof. These compounds have nonkaliuretic diuretic activity at oral doses of 30 to 500 mg/kg or approximately 20%–100% of these amounts by intramuscular or subcutaneous administration. The specific nonkaliuretic diuretic effect of these compounds is totally unexpected when considered in the light of the lack of diuretic activity of the unsubstituted 2,4-di-amino-7-phenyl-pteridine.

The compounds of the present invention are made by condensing, in a hot aqueous medium, 4,5,6-triaminopyrimidine sulfate with the appropriately ring-substituted phenylglyoxal. The reaction usually is instantaneous, and the pteridine formed precipitates. To optimize the yield, the mixture is best stirred for 30 minutes at a temperature between room temperature and the boiling point of the mixture. Before removal of the pteridine, it is advantageous to lower the temperature of the condensation mixture to 0–5 degrees C.

In order to illustrate the procedure for making the compounds of the present invention, reference is made to the following examples which, however, are not intended to limit the invention in any way.

EXAMPLE 1

4-Amino-7-Phenylpteridine

To a hot solution of 6.45 g. of sodium acetate in 40 ml. of water was added 3.26 g. of 4,5,6-triaminopyrimidine sulfate. While stirring, 3.04 g. of phenylglyoxal monohydrate in 10 ml. of hot ethanol was added at once. A precipitate formed immediately. The mixture was stirred for 30 minutes at room temperature, cooled to 0 degrees C. and filtered. The solids collected were washed with 200 ml. of water, 100 ml. of acetone and finally with 100 ml. of ether to produce a dry yield of 1.1 g. (37% of theory) of 4-amino-7-phenylpteridine. After recrystallization from DMSO/water, the compound showed a melting point of 265–7 degrees C.

Oral administration of this compound at a dose of 100 mg/kg to 8 rats increases the 2-hour sodium excretion from 1.32 to 4.39 meq/kg; the corresponding values for potassium are 0.86 to 1.45 and for chlorine 1.51 to 4.48 meq/kg. Urine volume increases from 8.49 to 31.49 ml/kg. In all measurements given above, the first numbers indicate those of the control group with both control and test groups receiving 50 ml. per kg. of body weight of 0.9% saline and the drug vehicle, said vehicle being a 0.5% aqueous methylcellulose solution at a rate of 2 ml/kg of body weight. The control group showed a Na/K excretion ratio of 1.58 while the drug test group showed this ratio at 3.16.

The cummulative 6-hour Na/K ratios are 2.10 for the control group (31.59 ml/kg urine volume) and 3.84 for the test group (65.94 ml/kg). In another group of animals, the cummulative 24 hour Na/K ratios were 2.45 (54.47 ml/kg urine) for the control and 2.93 (79.73 ml/kg urine) for the test group.

At a test dose of 30 mg/kg, the 0–2 hour test group results were 30.37 ml/kg (12.31) urine, 3.97 meq/kg (2.14) for Na, 1.37 meq/kg (0.90) for K, 4.03 meg/kg (2.37) for Cl, with a Na/K ratio of 2.93 (2.35 for the control group). The corresponding 0–6 hour values are 56.50 ml/kg (27.54) urine volume, 7.85 meq/kg (4.22) for Na, 2.53 meq/kg (1.64) for K, 7.83 meq/kg (4.75) for Cl and a 3.13 Na/K ratio (control 2.56); the 0–24 hours test figures were, in the same order, 67.62 (54.47) ml/kg; 9.64 (8.24) meq/kg; 3.60 (3.43) meq/kg; 9.21 (7.96) meq/kg with a Na/K ratio of 2.71 (2.45 for the control).

At doses of 10 and 3 mg/kg, respectively, the values measured were so similar to the control values that no useful diuretic effect can be ascribed to the drug, e.g., the 24-hour Na/K for the control group was 2.45 and 2.51 for the test group at 10 ml/kg.

EXAMPLE 2

4-Amino-7-(3-chlorophenyl)pteridine

To a suspension of 5.2 g. of selenous acid in 40 ml. of dioxane was added 3.09 g. of m-chloroacetophenone. The mixture was refluxed for 4 hours, filtered and the filtrate was evaporated to dryness. A hot suspension of 3.90 g. of this glyoxal in 15 ml. of ethanol was added to a stirred suspension of 3.26 g. of 4,5,6-triaminopyrimidine sulfate and the condensation product was worked up as in Example 1 to produce 1.6 g. of 4-amino-7-(3-chlorophenyl)pteridine, melting at 260–4 degrees C.

This compound was tested at 100 mg/kg by the procedure of Example 1, giving the excretion rates shown in Table I.

Table I

|  | Control | | Compound | |
| --- | --- | --- | --- | --- |
|  | 0–2 hrs. | 0–6 hrs. | 0–2 hrs. | 0.6 hrs. |
| Urine vol. | 11.13 | 29.62 | 28.21 | 58.77 ml/kg |
| Sodium | 1.62 | 3.86 | 3.45 | 7.77 meq/kg |
| Potassium | 0.94 | 2.01 | 1.24 | 2.69 meq/kg |
| Chloride | 1.85 | 4.41 | 3.50 | 7.38 meq/kg |
| Na/K ratio | 1.71 | 1.92 | 2.77 | 2.90 |

EXAMPLE 3

4-Amino-7-(p-tolyl)pteridine

By treating 4-methylacetophenone with selenous acid as in Example 2 and subsequent treatment of the aldehyde in accordance with Example 2 with the equimolar amount of 4,5,6-triaminopyrimidine sulfate, produced a yield of 1.9 g. of 4-amino-7-(p-tolyl)pteridine, melting at 315 degrees (DMSO/water). The excretion values, obtained by the previously described method, produced the results shown in Table II.

Table II

| | Control | | Drug | |
|---|---|---|---|---|
| | 0–2 hrs. | 0–6 hrs. | 0–2 hrs. | 0–6 hrs. |
| Urine vol. | 6.89 | 22.04 | 21.57 | 43.97 ml/kg |
| Na | 1.04 | 3.16 | 2.77 | 5.94 meq/kg |
| K | 0.77 | 1.70 | 1.09 | 2.14 meq/kg |
| Cl | 1.28 | 3.78 | 2.88 | 6.09 meq/kg |
| Na/K ratio | 1.47 | 1.99 | 2.48 | 2.80 |

EXAMPLE 4

4-Amino-7-(m-tolyl)pteridine

Using 3-methylacetophenone in place of the p-analog of Example 3 produced 0.9 g. of 4-amino-7-(m-tolyl)-pteridine, melting at 248–250 degrees C. The test results are shown in Table III.

Table III

| | Control | | Drug | |
|---|---|---|---|---|
| | 0–2 hrs. | 0–6 hrs. | 0–2 hrs. | 0–6 hrs. |
| Urine vol. | 10.42 | 26.01 | 19.51 | 41.35 ml/kg |
| Na | 1.27 | 3.28 | 2.43 | 5.42 meq/kg |
| K | 0.79 | 1.64 | 1.16 | 2.15 meq/kg |
| Cl | 1.56 | 4.03 | 2.74 | 5.88 meq/kg |
| Na/K ratio | 1.57 | 2.00 | 2.39 | 2.53 |

EXAMPLE 5

4-Amino-7-(4-dimethylaminophenyl)pteridine

Oxidation of p-N,N-dimethylaminoacetophenone with selenous acid and subsequent reaction of 3.9 g. of th aldehyde with 3.26 g. of 4,5,6-triaminopyrimidine sulfate according to Example 1 produced 2.2 g. of 4-amino-7-(4-dimethylaminophenyl)pteridine, which decomposes at 275 degrees C. The test results are shown in Table IV.

Table IV

| | Control | | Drug | |
|---|---|---|---|---|
| | 0–2 hrs. | 0–6 hrs. | 0–2 hrs. | 0–6 hrs. |
| Urine vol. | 6.88 | 22.04 | 18.71 | 51.07 mg/kg |
| Na | 1.04 | 3.16 | 1.66 | 5.62 meq/kg |
| K | 0.77 | 1.67 | 0.67 | 1.72 meq/kg |
| Cl | 1.28 | 3.78 | 1.91 | 6.14 meq/kg |
| Na/K | 1.47 | 1.99 | 2.34 | 3.23 |

When using the corresponding o- or m-dimethylamino acetophenone in place of the above p-analog, essentially identical test results are obtained.

The compounds of the present invention are preferably used in oral dosage forms such as tablets, capsules, wafers, elixirs, syrups and the like. For liquid forms, the above compounds are suspended in an aqueous medium containing the customary flavoring and coloring agents. Since these compounds are essentially insoluble in water, dispersing and/or suspending agents acceptable for human consumption are used together with suspension stabilizers. For the various solid dosage forms, the usual solid diluents are used where required. Capsules can be filled with undiluted powdered or granulated crystals of the new compounds. For tablets, the following standard procedure may be used:

About one-half of 52 g. of cornstarch is milled together with 100 g. of the new drug and 220 g. of calcium phosphate dibasic dihydrate. This blend is milled until homogenous and passed through a 40-mesh screen. The remaining portion of the cornstarch is granulated with water, heated and mixed with the above drug blend in a hot air oven at 50 degrees C. and sifted through a 16-mesh screen. These granules are then mixed with 16 g. of talcum powder, 4 g. of magnesium stearate and 0.8 g. of combined coloring and flavoring additives. The mixture is blended homogeneity, passed through a 30-mesh screen and blended for another 15 minutes. This blend is compressed into tablets weighing approximately 400 mg. using a 9/32" standard convex punch resulting in tablets of a hardness of 7–9 with each tablet containing 100 mg. of the drug. In a similar fashion, tablets weighing 650 mg. containing 250 mg. of drug can be prepared, preferably in a tableting machine producing bisected tablets.

The compounds of the present invention exhibit no toxic symptoms. An oral $LD_{50}$ could not be established as the test animals show no changes at doses of up to 2 g/kg. This phenomenon is probably based on the low solubility of the drugs which makes it even more surprising that such a pronounced, nonkaliuretic diuretic effect is obtained at doses of 50 mg/kg and above.

A practical range for daily oral administration is between 30 and 500 mg/kg with a preferred range being 50–250 mg/kg. These amounts are based on the free amine. However, it is to be understood that pharmaceutically acceptable acid addition salts can be used in place of the free amine, e.g., the hydrochloride, sulfate, phosphate, citrate, succinate, acetate and the like.

We claim:

1. A compound of the formula

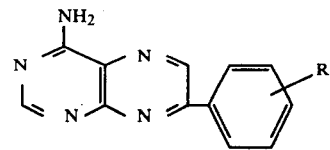

wherein R is hydrogen, dimethylamino, m-methyl or p-methyl.

2. The compound of claim 1 wherein R is hydrogen.
3. The compound of claim 1 wherein R is m-methyl.
4. The compound of claim 1 wherein R is N,N-dimethylamino.
5. The compound of claim 4 wherein said N,N-dimethylamino group is in the p-position.
6. The compound of claim 1 wherein R is p-methyl.
7. The method of increasing the urine excretion in a warm-blooded animal consisting essentially in administering to said animal a diuretically sufficient amount of a compound of a formula

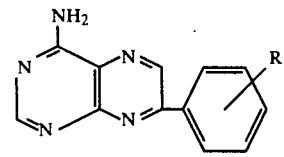

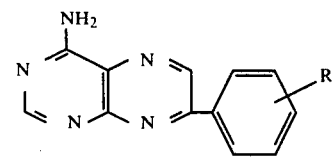

wherein R is H, Me₂N, m-Me or p-Me.

8. The method of claim 7 wherein said amount is a daily dose of between 30 and 500 mg./kg.

9. The method of claim 7 wherein said amount is a daily dose of betwwen 50 and 250 mg./kg.

10. The method of claim 9 wherein R is hydrogen.

11. The method of claim 9 wherein R is m-Me.

12. The method of claim 9 wherein R is Me₂N.

13. The method of claim 12 wherein said Me₂N is in the p-position.

14. The method of claim 9 wherein R is p-Me.

15. A medicinal composition for increasing urine excretion from a warm-blooded animal containing a diuretically effective amount of a compound of the formula

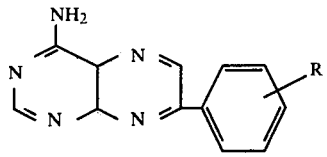

wherein R is H, Me₂N, m-Me or p-Me together with a pharmaceutically acceptable diluent or carrier.

16. The composition of claim 15 in the form of a tablet for oral administration.

17. The composition of claim 16 wherein R is hydrogen.

18. The composition of claim 16 wherein R is Me₂N.

19. The composition of claim 18 wherein said Me₂N is in the p-position.

20. The composition of claim 16 wherein R is p-Me.

21. The composition of claim 16 wherein R is m-Me.

* * * * *

UNITED STATES PATENT OFFICE
CERTIFICATE OF CORRECTION

PATENT NO. : 4,187,307
DATED : February 5, 1980
INVENTOR(S) : G. Y. Paris, et al.

It is certified that error appears in the above-identified patent and that said Letters Patent are hereby corrected as shown below:

In column 4, line 51, Claim 7, after "of", delete "a" and substitute therefor -- the --.

In column 4, line 55, Claim 7, delete the following formula

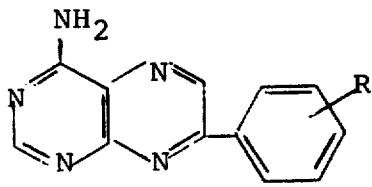

Signed and Sealed this

Twenty-ninth Day of April 1980

[SEAL]

Attest:

SIDNEY A. DIAMOND

Attesting Officer

Commissioner of Patents and Trademarks